(12) United States Patent
Achard de la Vente

(10) Patent No.: US 12,616,825 B2
(45) Date of Patent: May 5, 2026

(54) IMPLANTABLE ACCESS DEVICE FOR ACCESSING THE VASCULAR SYSTEM OF A HUMAN OR ANIMAL BODY, PARTICULARLY SUBCUTANEOUSLY IMPLANTABLE ACCESS PORT

(71) Applicant: PFM MEDICAL GMBH, Cologne (DE)

(72) Inventor: Stanislas Marie Bertrand Achard de la Vente, La Chaux de Fonds (CH)

(73) Assignee: PFM Medical GmbH (DE)

( * ) Notice: Subject to any disclaimer, the term of this patent is extended or adjusted under 35 U.S.C. 154(b) by 882 days.

(21) Appl. No.: 17/051,589

(22) PCT Filed: Apr. 18, 2019

(86) PCT No.: PCT/EP2019/060116
§ 371 (c)(1),
(2) Date: Oct. 29, 2020

(87) PCT Pub. No.: WO2019/211101
PCT Pub. Date: Nov. 7, 2019

(65) Prior Publication Data
US 2021/0093846 A1 Apr. 1, 2021

(30) Foreign Application Priority Data
Apr. 29, 2018 (EP) ..................................... 18169997

(51) Int. Cl.
*A61M 39/02* (2006.01)
(52) U.S. Cl.
CPC . *A61M 39/0208* (2013.01); *A61M 2039/0232* (2013.01); *A61M 2205/581* (2013.01); *A61M 2205/582* (2013.01)

(58) Field of Classification Search
CPC ...... A61M 39/0208; A61M 2039/0232; A61M 2205/581; A61M 2205/582;
(Continued)

(56) References Cited

U.S. PATENT DOCUMENTS

| 3,196,839 A | 7/1965 | Bertoglio et al. |
| 4,861,341 A | 8/1989 | Woodburn |
| | (Continued) | |

FOREIGN PATENT DOCUMENTS

| DE | 809514 | 7/1951 |
| DE | 812404 | 8/1951 |
| | (Continued) | |

OTHER PUBLICATIONS

Office Action from related Japanese Appln. No. 2021-508066, dated Dec. 13, 2022. English translation attached.
(Continued)

*Primary Examiner* — Chelsea E Stinson
*Assistant Examiner* — Hamza A Darb
(74) *Attorney, Agent, or Firm* — Lisa E. Geary; Eckert Seamans Cherin & Mellott LLC

(57) ABSTRACT

Implantable access device for accessing the vascular system of a human or animal body, particularly subcutaneously implantable access port, comprising: a port body with at least one outlet opening connected or connectable to a catheter for accessing the vascular system of the human or animal body, a needle entrance with at least one inlet opening for receiving a needle, wherein the needle entrance is connected to the port body and movable relative to the port body between a first, unactuated operating condition and a second, actuated operating condition, and locking means for locking the needle entrance in the first, unactuated operating condition and in the second, actuated operating condition, wherein the locking means are activated by
(Continued)

inserting the needle into the needle entrance and applying a predetermined movement to needle entrance via the inserted needle and/or by applying a predetermined movement to the needle entrance via the inserted needle and removing the needle from the needle entrance.

19 Claims, 7 Drawing Sheets

(58) Field of Classification Search
CPC .......... A61M 5/14276; A61M 2210/12; A61M 2039/022; A61M 2039/0226; A61M 2039/0258; A61M 2039/0261; A61M 2039/0273
See application file for complete search history.

(56) References Cited

U.S. PATENT DOCUMENTS

| | | | |
|---|---|---|---|
| 5,350,360 A | 9/1994 | Ensminger et al. | |
| 5,352,204 A | 10/1994 | Ensminger | |
| 5,356,381 A | 10/1994 | Ensminger et al. | |
| 5,741,228 A * | 4/1998 | Lambrecht ........ | A61M 39/0208 |
| | | | 251/149.3 |
| 5,848,989 A | 12/1998 | Villani | |
| 5,911,706 A | 6/1999 | Estabrook et al. | |
| 6,007,516 A | 12/1999 | Burbank et al. | |
| 6,056,717 A | 5/2000 | Finch et al. | |
| 6,120,492 A | 9/2000 | Finch et al. | |
| 6,193,684 B1 | 2/2001 | Burbank et al. | |
| 6,454,170 B1 | 9/2002 | Feeser | |
| 6,506,182 B2 | 1/2003 | Estabrook et al. | |
| 6,565,525 B1 * | 5/2003 | Burbank ............. | A61M 1/3659 |
| | | | 604/93.01 |
| 7,056,316 B1 | 6/2006 | Burbank et al. | |
| 2005/0131325 A1 * | 6/2005 | Chen ................. | A61M 39/0208 |
| | | | 602/41 |
| 2005/0203484 A1 | 9/2005 | Nowak | |
| 2007/0016162 A1 * | 1/2007 | Burbank ........... | A61M 39/0208 |
| | | | 604/288.03 |
| 2010/0274223 A1 | 10/2010 | Teitelbaum et al. | |
| 2010/0286615 A1 * | 11/2010 | Gyrn ................. | A61M 25/0612 |
| | | | 604/164.08 |

FOREIGN PATENT DOCUMENTS

| | | |
|---|---|---|
| DE | 1267570 | 5/1968 |
| DE | 19624320 | 10/1997 |
| EP | 0332943 | 9/1989 |
| EP | 1016431 | 7/2000 |
| EP | 1629862 | 3/2006 |
| EP | 1765456 | 11/2011 |
| GB | 2192338 | 1/1988 |
| JP | 8501008 | 2/1996 |
| JP | 2001509061 | 7/2001 |
| WO | 98/314416 | 7/1998 |
| WO | 98/55167 | 12/1998 |
| WO | 01/21251 | 3/2001 |

OTHER PUBLICATIONS

International Search Report from corresponding PCT Appln. No. PCT/EP2019/060116, dated Jun. 26, 2019.
Written Opinion from corresponding PCT Appln. No. PCT/EP2019/060116, dated Jun. 26, 2019.

* cited by examiner

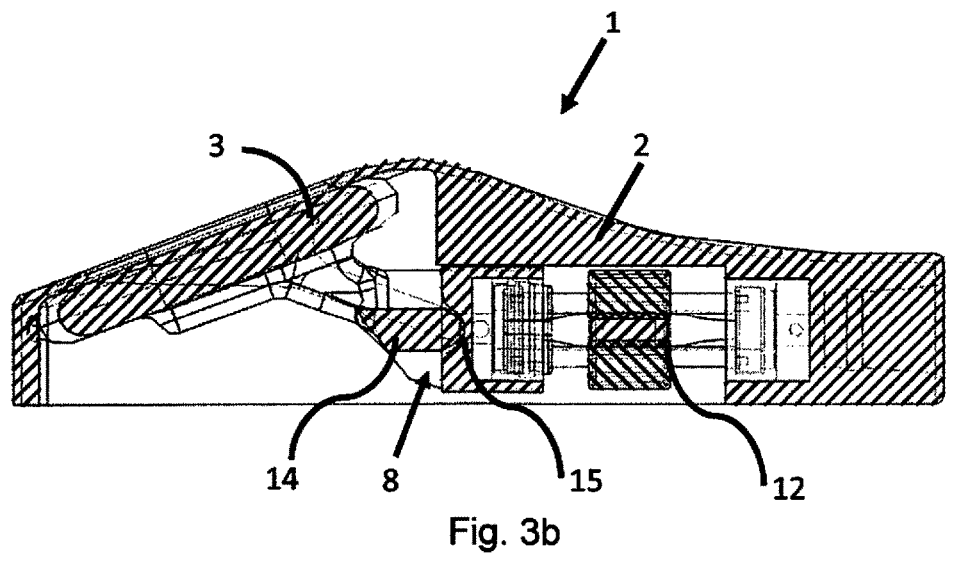
Fig. 3b
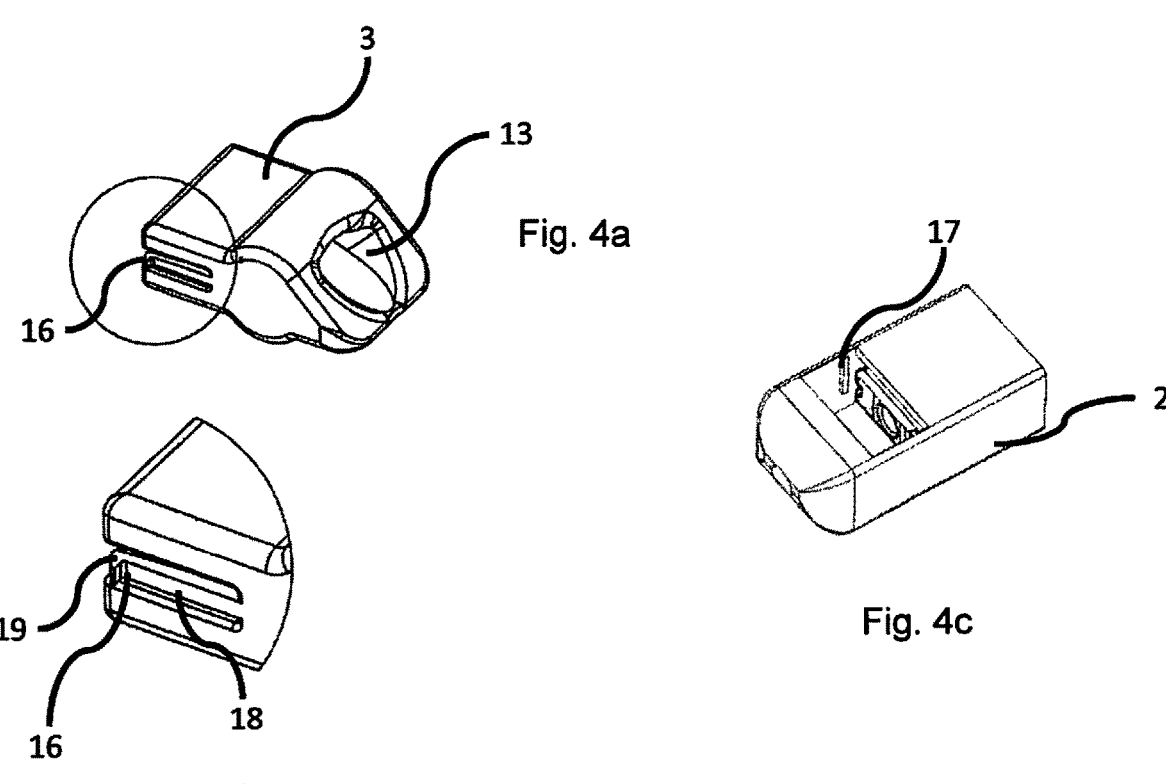
Fig. 4a
Fig. 4b
Fig. 4c

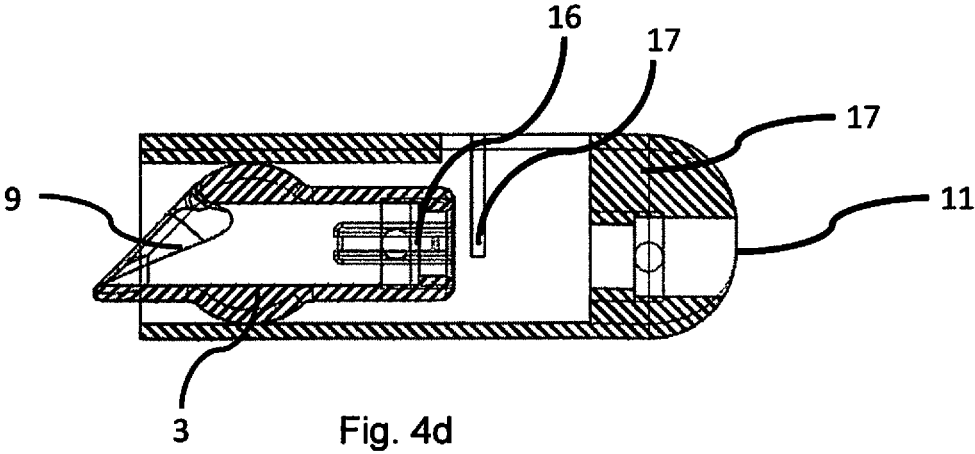
Fig. 4d
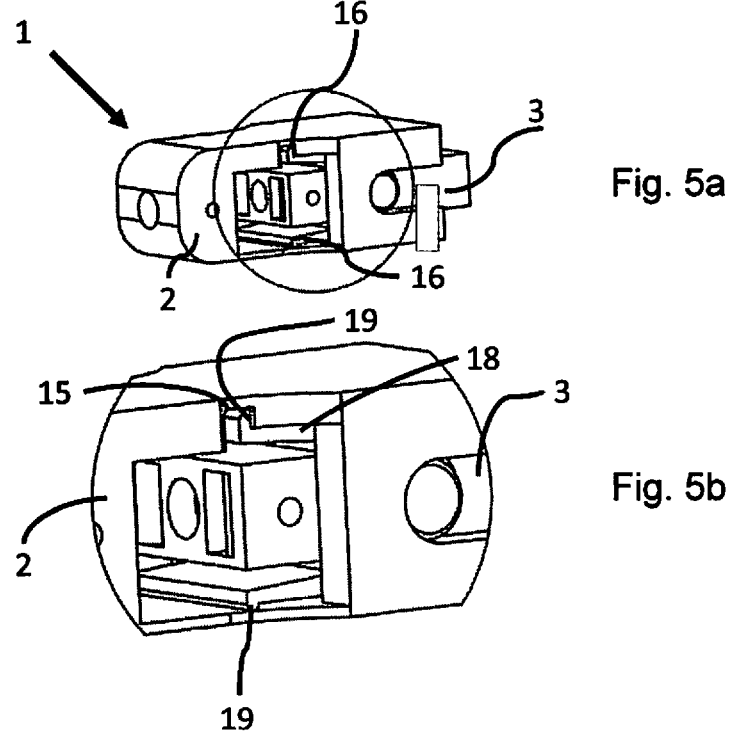
Fig. 5a
Fig. 5b

IMPLANTABLE ACCESS DEVICE FOR ACCESSING THE VASCULAR SYSTEM OF A HUMAN OR ANIMAL BODY, PARTICULARLY SUBCUTANEOUSLY IMPLANTABLE ACCESS PORT

FILED

The invention relates to an implantable access port for accessing the vascular system of a human or animal body, particularly subcutaneously implantable access port.

BACKGROUND

During a medical treatment it is sometimes necessary to repeatedly access the vascular system of a human or animal body, for example for infusing therapeutic agents, drugs or such the like, removing body fluids, treating body fluids, injecting contrast agents and/or insertion of medical devices such as cameras, ultra-sound probes, brushes, catheters, catching devices or similar devices. In case of fluid exchange therapies, like for example hemodialysis, hemo-filtration, hemodiafiltration, plasmapheresis, ultrafiltration, aquafiltration, n lipid pheresis, hemoperfusion, peritoneal dialysis or the like, devices for accessing the vascular system of a human or animal body which allow a high-volume fluid flow are preferred.

From the prior art a variety of strategies are known for accessing the vascular system of a human or animal body, like for example direct vessel cannulation, short and long term catherization and implantation of subcutaneous port systems.

A temporary access to the vascular system of the human or animal body can be simply provided by a direct percu-taneous introduction of a needle through the skin of the human or animal body into a vessel of the vascular system of the human or animal body. Such an approach is the least expensive and simplest form of accessing the vascular system of the human or animal body and is particularly suitable for short term applications like for example intra-venous drug delivery, removal of blood or the like. However, repeated introduction of a needle through the skin of the human or animal body into a vessel of the vascular system of the human or animal body can result in vessel thrombosis, stenosis and formation of pseudo-aneurisms, as well as infections.

Transcutaneous devices, like short and long-term cath-eters, are used to address the problems of repeated direct percutaneous introduction of a needle through the skin of the human or animal body into a vessel of the vascular system of the human or animal body. Such transcutaneous devices can be flexible cannulae, which are inserted percutaneously into the region of interest such as a blood vessel or cavity in the human or animal body. However, although transcutane-ous devices deal with the problems of a direct percutaneous introduction of a needle through the skin of the human or animal body into a vessel of the vascular system of the human or animal body they often cause complications due to infections. The infection usually infects the point where the device passes through the skin of the human or animal body or even the vascular system of the human or animal body itself. Thus, such transcutaneous devices can cause local or even systemic infections.

Therefore a direct percutaneous introduction of a needle through the skin of the human or animal body into a vessel of the vascular system of the human or animal body or use of a transcutaneous catheter are not well suited for long term applications or for extracorporeal procedures that must be repeated periodically, like for example hemodialysis, hemo-filtration, hemodiafiltration, plasmapheresis, ultrafiltration, aquafiltration, n lipid pheresis, hemoperfusion, peritoneal dialysis or the like.

To deal with the above problems varieties of subcutane-ously implanted ports have been proposed over the years for long term and/or periodically repeated accesses to the vas-cular system of the human or animal body. A typical subcutaneously implanted port has an access region for receiving a needle or access catheter, a fluid flow path through the port and a subcutaneously catheter attached to a vessel of the vascular system of the human or animal body. Thus, a fluid flow path is provided from the access catheter through the subcutaneously implanted port and the subcu-taneously catheter to the vascular system of the human or animal body.

The most common type of subcutaneously implanted ports, like for example disclosed in U.S. Pat. No. 6,056,717, comprises a housing with a port chamber for receiving an introduced needle. The surface of the port chamber next to the skin of the human or animal body is enclosed by a high-density self-sealing septum, typically made of silicone rubber. A subcutaneously implanted catheter, which com-municates with a vein or other site within the human or animal body, is connected and in fluid connection to the port chamber. Implantation of such devices generally proceeds by making a small subcutaneous pocket in an appropriate area of the human or animal body under local anaesthesia. The subcutaneously implanted catheter is tunnelled to the desired infusion site.

Since the septum faces towards the skin of the human or animal body and the subcutaneously implanted catheter runs substantially parallel to the skin of the human or animal body, there exists a 90° bend in the flow path from the introduced needle, which is perpendicular to the skin of the human or animal body, to the subcutaneously implanted catheter. Especially for high flowrates this can result in damages to the blood, so-called hemolysis.

To avoid damaging or coring of the septum a special needle, like so-called port or Huber needle, is introduced through the skin of the human or animal body and the septum into the port chamber. Damaging or coring of the septum is avoided by a special cut of the needle. After the medical treatment has been finished the needle is withdrawn from the port chamber.

Since large diameter needles can damage the rubber septum used for sealing the port chamber the fluid flow rate is limited for these known subcutaneously implanted port devices. Further, it is desirable to limit the height of the subcutaneously implanted port because of optical reason and the local stress imposed on the skin of the human or animal body. However, this results in a limited height of the port chamber as well as a thinner port septum; so a small displacement of the introduced needle can cause an easier retraction of the needle out of the port chamber because of friction reduction induced by the thinner septum. In case where toxic materials are being infused, like during chemo-therapy, the retraction of the needle out of the port chamber can cause local tissue damage, which may lead to further surgical treatments like corrective surgery or removal of tissue.

Moreover, due to the at least one 90° bend in the fluid flowing path it is difficult or even impossible to clear the subcutaneously implanted port if e.g. thrombosis occurs. A thrombus can result in serious patient injuries like e.g. pulmonary embolism or even blockage. To clear a subcutaneously implanted port it is necessary to feed a cleaning wire through the hypodermic needle into the port chamber and further through the subcutaneously implanted catheter. However, it is very difficult to feed the cleaning wire from the port chamber into the subcutaneously implanted port due to the at least one 90° bend. In case the subcutaneously implanted port cannot be cleaned it has to be replaced to avoid the risk of serious patient injuries.

To overcome the problems associated with the perpendicular introduction of the needle into the port chamber it has been proposed for example in DE 196 24 320 C1, EP 0 332 943 81, EP 1 629 862 A1, EP 1 765 456 81, U.S. Pat. No. 5,848,989 or U.S. Pat. No. 4,861,341 to use a tube shaped subcutaneously implanted port, wherein the septum is arranged in such a way that the needle is introduced substantially parallel to the skin of the human or animal body. This result in a substantially straight fluid flowing path through the subcutaneously implanted port. Due to the substantially straight fluid flowing path a cleaning wire or another device can be easily introduced through the port chamber into the subcutaneously implanted catheter. Further, the length of the catheter housing can be enhanced without causing more stress to the skin in the area of the implantation site. Thus, the length of the port chamber can be enhanced and the needle can be introduced further into the port chamber and thereby significantly reducing the risk of an accidental retraction of the needle out of the port chamber.

Further, it is known from the prior art, like example from U.S. Pat. Nos. 6,007,516, 6,120,492 6,193,684 B1 and 7,056,316 B1, to replace the septum by a valve assembly. Due to the valve assembly fistula needles can be introduced into the subcutaneously implanted port without damaging any septum. Usually the valve is actuated by moving a part of the valve by the introduced needle or by advancing the introduced needle through the valve, like e.g. through a leaflet valve assembly. This even allows to use larger diameter needles, which increases the maximum achievable fluid flowing rate. U.S. Pat. No. 6,565,525 B1 further discloses a dual port vascular access assembly comprising first and second access ports. This vascular access assembly is designed to close the second access port in the absence of an access tube in the first access port. Thus, blood withdrawal will be automatically terminated upon cessation of blood returned to due to loss of the return access tube in the first access port. However, according to the aforementioned prior art documents the needles are introduced perpendicular to the skin of the human or animal body and thus, they still suffer from the above-mentioned problems associated with the perpendicular introduction of the needle into the port chamber.

U.S. Pat. No. 5,350,360, EP 1 016 431 A1, U.S. Pat. Nos. 5,741,228, 5,356,381 and 5,352,204 each disclose a subcutaneously implantable access port with a housing having a funnel shaped inlet orifice leading to a reduced diameter guide passageway. An articulating valve, which may take various forms including leaflet type valves or self-collapsing tubular valves, are placed in line with the access port housing. An external filament such as a needle, guide wire, optical fibre, or external catheter can be introduced into the access device and fed through the housing to penetrate the articulating valve.

U.S. Pat. Nos. 5,911,706 and 6,506,182 B2 each disclose an implantable single or dual-lumen device for repeated accessing vessels within a human or animal body. The device uses a resilient material to form a seal and has a smooth streamlined flowpath with no flow discontinuity.

The device is joined to a subcutaneously implanted catheter, such that fluids can be extracted from or injected into the vessel to be accessed. The device is designed for the high flowrates, on the order of 150 and greater millilitres per minute, associated with fluid exchange therapies. A smooth flow streaming is important to minimize damage to the blood. A corresponding straight-needle apparatus is designed to mate and lock with the access device, where alignment and open flowpath is ensured. A valve seal incorporates opposing very hard surfaced guide elements that are retained and in intimate contact with the seal itself. The needle assembly pushes open these guide elements which open the seal before the needle point reaches the seal material.

Especially in case of fluid exchange therapies, like for example hemodialysis, hemofiltration, hemodiafiltration, plasmapheresis, ultrafiltration, aquafiltration, n lipid pheresis, hemoperfusion, peritoneal dialysis or the like, which require a high-volume fluid flow there is a need of devices for accessing the vascular system of a human or animal body which guarantee that the maximum fluid flow rate is achieved. Further, since fluid exchange therapies usually need more than one hour the device for accessing the vascular system together with the inserted needle should be as comfortable as possible for the patient, i.e. have a low profile and be as close as possible to the skin of the patient.

SUMMARY

These objects are solved according to the invention by an implantable access device for accessing the vascular system of a human or animal body, particularly subcutaneously implantable access port, comprising:

a port body with at least one outlet opening connected or connectable to a catheter for accessing the vascular system of the human or animal body, a needle entrance with at least one inlet opening for receiving a needle, wherein the needle entrance is connected to the port body and movable relative to the port body between a first, unactuated operating condition and a second, actuated operating condition, and locking means for locking the needle entrance in the first, unactuated operating condition and in the second, actuated operating condition, wherein the locking means are activated by inserting the needle into the needle entrance and applying a predetermined movement to needle entrance via the inserted needle and/or by applying a predetermined movement to the needle entrance via the inserted needle and removing the needle from the needle entrance.

According to the invention the passageway through the implantable access device, i.e. from the inserted needle, through the port body and catheter attached to the outlet opening of the port body, is completely closed in the first, unactuated operating condition and completely opened in the second, actuated operating condition. Therefore, for example the port body comprises a valve mechanism which is actuated, i.e. opened and closed, by the relative movement of the needle entrance to the port body.

Since the locking means of the inventive implantable access device are activated by inserting the needle into the needle entrance the inserted needle can be moved closer to the skin of the patient by the relative movement of the needle entrance with the inserted needle to the port body. Thus, in the second, activated operating condition the needle inserted in the needle entrance has moved closer to the skin of the patient and thereby enhancing the comfort during the medical treatment.

Since the locking means are locked in the first, unactuated operating condition respectively the second, actuated operating condition it is guaranteed that the passageway through the inventive implantable access device is either completely closed or completely opened. Thus, the locking means have two stable operating conditions, so-called bi-stable mechanism.

According to a variant of the invention the implantable access device further comprises blocking means which block a relative movement of the needle entrance to the port body in case no needle has been inserted into the needle entrance. Thus, an accidental actuation of the implantable access device, i.e. movement of the needle entrance from the first, unactuated operating condition to the second, actuated operating condition is prevented.

In a preferred variant of the invention the predetermined movement of the needle entrance at least partially differs from the movement of the needle for inserting the needle into the needle entrance. Thus, the movement of inserting the needle into the needle entrance alone cannot actuated the implantable access device, i.e. move the needle entrance from the first, unactuated operating condition to the second, actuated operating condition. For such an actuation the person who inserted the needle into the needle entrance of the implantable access device must at least partially change the movement. In this way an accidental actuation during insertion of the needle into the needle entrance is prevented.

Pursuant to an advantageous variant of the invention the predetermined movement of the needle entrance comprises a pivoting and/or translational movement of the needle entrance. Preferably the predetermined movement of the needle entrance comprises a pivoting and translational movement. For example, first the needle entrance must be slightly moved translational to enable a pivoting movement and after the pivoting movement the needle entrance is locked in the other operating condition by another translational movement. Thus, first the operating condition is unlocked by a translational movement, then the needle entrance and the needle therein is pivoted closed to the skin of the patient and afterwards the needle entrance is locked in the other operating condition by another translational movement.

In a variant of the invention the insertion angle of the needle entrance, in which the needle is inserted into the needle entrance, is between 15° and 40°, preferably between 25° and 30°. In this range it is easy to insert the needle into the needle entrance and to provide a streamlined flowpath through the implantable access device and to conform the inserted needle close to the skin of the patient in the second, actuated operating condition.

In a further preferred variant, the needle entrance comprises a funnel to guide the needle into the needle entrance.

According to variant of the invention the locking means comprise a cam on the needle entrance and a corresponding recess for guiding the cam on the port body and/or a cam on the port body and a corresponding recess for guiding the cam on the needle entrance. Using such cam and recess means the relative movement between the needle entrance and the port body can be defined and guided.

Pursuant to a preferred variant of the invention the cam is shaped rectangular or triangular, preferably with rounded corners. A rectangular or triangular cam is easy to manufacture by e.g. injection molding or such the like and provided a good stability. The rounded corners avoid blocking or jamming of the cam in the recess for guiding the cam.

According to a variant of the invention the recess has at least one, preferably two, pits for receiving the cam either in the first, unactuated operating condition or in the second, actuated operating condition. Thus, the cam can be locked in the first and/or second operating condition by moving the cam in the pit of the recess. A recess for guiding the cam with two recesses is according to a preferred variant of the invention heart shaped.

In a preferred embodiment of the invention the locking means comprise a ballpoint pen mechanism or a SD-slot mechanism for locking the needle entrance in the first, unactuated operating condition and in the second, actuated operating condition. Alternatively, the locking means comprise a snap fit connection, preferably a snap on the needle entrance and at least one recess or protrusion on the port body for receiving or engaging with the snap, for locking the needle entrance in the first, unactuated operating condition and in the second, actuated operating condition. Such mechanisms are generally referred to as push-push-locking mechanisms and are known from the prior art in many different designs, like e.g. DE809514, DE812404, DE1267570, U.S. Pat. No. 6,454,170, for several decades.

According to a preferred variant of the invention the locking means comprise a spring for locking the locking means in the first, unactuated operating condition and in the second, actuated operating condition. Thus, bi-stable system is achieved and only a partial opening of the passageway through the implantable access port is avoided. This is particularly advantageous for fluid exchange therapies which require a high flowrate.

In a particularly preferred variant the spring is connected to or integrally formed with the valve mechanism of the implantable access device. Thus, the first unactuated operating condition of the needle entrance is directly connected to the first, unactuated operating condition of the valve mechanism and the second, actuated operating condition of the needle entrance is directly connected to the second, actuated operating condition of the valve mechanism.

According to a particular advantageous variant of the invention the locking means create an audio and/or haptic feedback, like a sound and/or vibration, when being locked in the first, unactuated operating condition and/or in the second, actuated operating condition.

As described above it is advantageous to have an implantable access device for accessing the vascular system of a human or animal body, particularly subcutaneously implantable access port, comprising:

a port body with at least one outlet opening connected or connectable to a catheter for accessing the vascular system of the human or animal body, and a needle entrance with at least one inlet opening for receiving a needle, wherein the needle entrance is connected to the port body and movable relative to the port body between a first, unactuated operating condition and a second, actuated operating condition.

One problem associated with needle entrance that is movable relative to the port body between a first, unactuated operating condition and a second, actuated operating condition is that the tissue surrounding the implantable access device can be pinched during the relative movement between the needle entrance and the port body, which can be unpleasant for the patient. Further, the tissue surrounding the implantable access device can block the relative movement between the needle entrance and the port body.

It is thus an object of the present invention to provide an implantable access device for accessing the vascular system of a human or animal body, particularly subcutaneously implantable access port, comprising a port body with at least one outlet opening connected or connectable to a catheter for accessing the vascular system of the human or animal body, and a needle entrance with at least one inlet opening for receiving a needle, wherein the needle entrance is connected to the port body and movable relative to the port body between a first, unactuated operating condition and a second, actuated operating condition that avoids the aforementioned problems.

According to the present invention the object is solved in that the implantable access device for accessing the vascular system of a human or animal body, particularly subcutaneously implantable access port, further comprises a flexible socket arranged between the port body and the needle entrance and at least covering the area or volume where the needle entrance moves relative to the port body to prevent tissue growth in this area. Since the area or volume where a relative movement between needle entrance and the port body takes place is covered by the flexible socket a pinching of tissue is avoided. Further, no tissue can grow in this area because it is already covered by the flexible socket.

The flexible socket is designed such that the flexible socket is deformed by the relative movement between needle entrance and the port body. By this deformation of the flexible socket the surrounding tissue will be pushed out of the moving path and thereby avoiding any pinching of tissue. According to the invention the flexible socket can be at least deformed in such a way that the flexible socket has no negative impact on the relative movement between the needle entrance and the port body, i.e. the complete desired relative movement between the needle entrance and the port body is possible.

According to a variant of the present invention the flexible socket has a first opening for connecting the flexible socket to the port body and a second opening for connecting the flexible socket to the needle entrance. The two openings of the flexible socket allow an easy assembly of the implantable access device for accessing the vascular system of a human or animal body, particularly subcutaneously implantable access port, comprising a port body and a needle entrance, wherein the needle entrance is connected to the port body and movable relative to the port body between a first, unactuated operating condition and a second, actuated operating condition.

In a further variant of the invention the flexible socket is hollow. A flexible and hollow socket has the advantage that the socket can be easily deformed during the relative movement of the needle entrance to the port body and at the same time prevents any pinching of tissue and/or tissue growth between the needle entrance and the port, especially in the area or volume of relative movement between these two parts. Further, this saves material costs during manufacturing.

In a preferred variant of the invention the first opening of the flexible socket is smaller than a corresponding portion of the port body, where the first opening of the flexible socket is connected to the port body. Since the socket is flexible and the first opening is smaller than the connecting portion of port body the first opening of the flexible socket is stretched during the connection to the connecting portion of the port body. This stretching of the first opening of the flexible socket creates a friction-force based connection between the flexible socket, particularly the first opening of the flexible socket, and the connecting portion of the port body. For example, the first opening of the flexible socket is about 10 to about 20% smaller than the connecting portion of the port body. This creates a sufficient connection between the first opening of the flexible socket and the connecting portion of the port body without any risk of damaging the first opening of the flexible socket due to overstretching. Further, such a first opening of the flexible socket provides a good sealing between the port body and the flexible socket.

According to a preferred variant of the invention the first opening of the flexible socket and the connecting portion of the port body have corresponding surfaces. The corresponding surfaces of the first opening of the flexible socket and the connecting portion of the port body have the advantage that the contact surface between the first opening of the flexible socket and the connecting portion of the port body is enhanced and thereby enhancing the friction force between the first opening of the flexible socket and the connecting portion of the port body.

In a particularly preferred variant of the invention the corresponding surfaces comprise protrusions and recesses, like a barbed fit. Such a barb fit allows an easy movement of the first opening of the flexible socket to the connecting portion of the port body in the assembly direction and prevents a movement of the flexible socket to the connecting portion of the port body in the opposite direction.

In an alternative variant of the invention the flexible socket, particularly the first opening of the flexible socket, is connected to the port body by clamping at least a part of the flexible socket between two corresponding parts of the port body. If the port body consists of at least two parts the flexible socket can be safely connected to the port body during manufacturing by clamping at a part of the flexible socket between the at least two parts of the port body. This also provides a good sealing between the port body and the flexible socket.

According to a variant of the invention the implantable access device further comprises a receptacle movably connected to the port body and wherein the needle entrance can be connected to the receptacle, so that the receptacle and the needle entrance are movable relative to the port body. In this variant the flexible socket at least covers the area or volume where the needle entrance and the receptacle move relative to the port body to prevent tissue growth in this area.

In a variant of the invention at least a part, preferably the second opening, of the flexible socket is clamped between corresponding surfaces of the receptacle and the needle entrance. In this way the flexible socket, particularly the second opening of the flexible socket, is securely connected to the implantable access device and any tissue growth in the area or volume of relative movement between the needle entrance and the receptacle to the port body is prevented. Further, this clamping of the flexible socket, especially the second opening of the flexible socket, between the receptacle and the needle entrance can be easily achieved during assembly of the inventive implantable access device.

In a further variant the flexible socket at least partially consists of silicone. A flexible silicone socket provides all the above-mentioned advantages and at the same time is easy and cheap to manufacture.

The invention further relates to a flexible socket that is configured and/or designed to be used with an implantable access device according to the invention.

BRIEF DESCRIPTION OF THE DRAWINGS

In the following the invention will be further explained with respect to embodiments shown in the figures, wherein

FIG. 3a, 3b show a cross-sectional view of an implantable access device with a movable needle entrance and a second embodiment of locking means;

FIG. 4a-4d show a third embodiment of locking means for an implantable access device;

FIG. 5a, 5b show a fourth embodiment of locking means for an implantable access device;

DETAILED DESCRIPTION

Figure 1A:
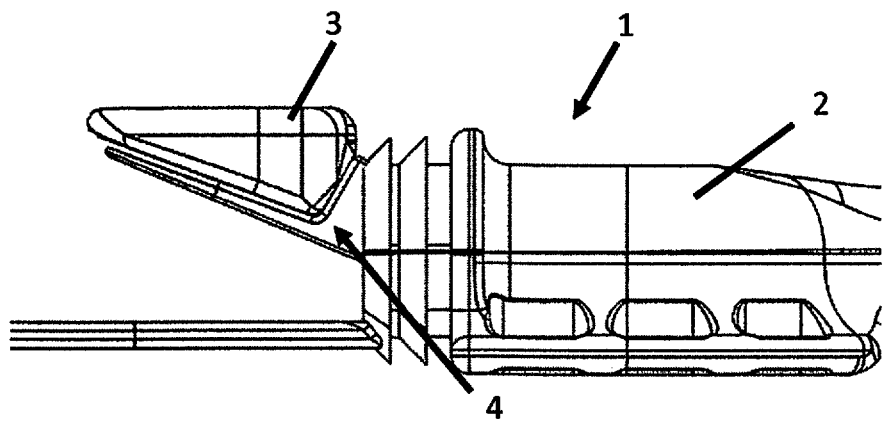
FIG. 1a shows a perspective view of an implantable access device in a first, unactuated operating condition.
Figure 1B:
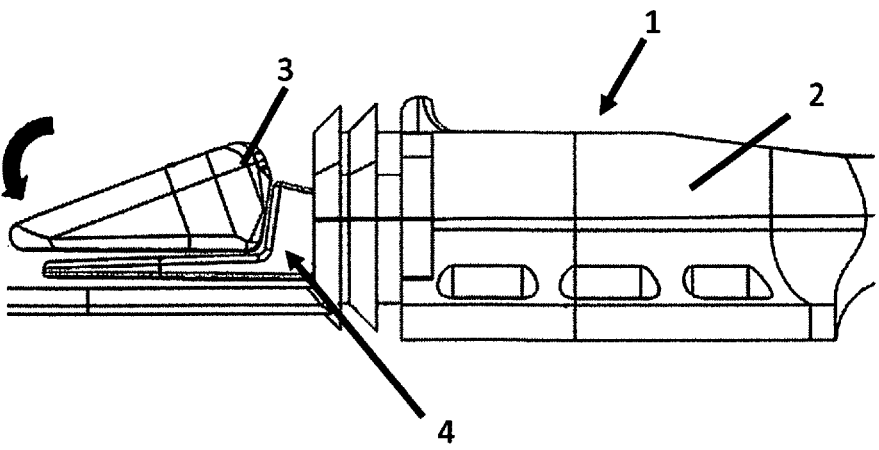
FIG. 1b shows the implantable access device from FIG. 1a in a second, actuated operating condition.

FIG. 1a shows a perspective view of an implantable access 1 for accessing the vascular system of a human or animal body, particularly subcutaneously implantable access port, in a first, unactuated operating condition. The implantable access device 1 comprises a port body 2 with at least one outlet opening connected or connectable to a catheter for accessing the vascular system of the human or animal body. The implantable access device 1 further comprises a needle entrance 3 with at least one inlet opening for receiving a needle. The needle entrance 3 is connected to the port body 2 via a receptacle 4. The needle entrance 3 and the receptacle 4 are movable relative to the port body 2 between a first, unactuated operating condition as shown in FIG. 1a and a second, actuated operating condition as shown in FIG. 1b.

In the first, unactuated operating condition the passageway through the implantable access port 1 is closed. Once a needle has been introduced into the needle entrance 3 the needle entrance 3 and the receptacle 4 are moved relative to the port body 2 from the first, unactuated operating condition into the second, actuated operating condition. In the second, actuated operating condition the passageway through the implantable access port 1 is opened and a fluid flow, in principle in both flow directions, through the needle and the implantable access port 1 is enabled. Furthermore, in the second, actuated operating condition the needle inserted into the needle entrance 3 is fixed in the needle entrance 2, for example by a friction force. After the treatment has been finished, the needle entrance 3 and the receptacle 4 are moved relative to the port body 2 from the second, actuated operating condition to the first, unactuated operating condition, thereby closing the passageway through the implantable access port 1 and at the same time releasing the needle from the needle entrance 3.

Preferably the needle entrance 3 and/or the receptacle 4 are pivotable relative to the port body 2 from the first, unactuated operating condition to the second, actuated operating condition. Further, in a variant of the invention it is possible that the needle entrance 3 and/or receptacle 4 can be fixed in the second, actuated operating condition by a translational movement of the needle entrance 3 and/or the receptacle 4 relative to the port body 2.

Figure 2:
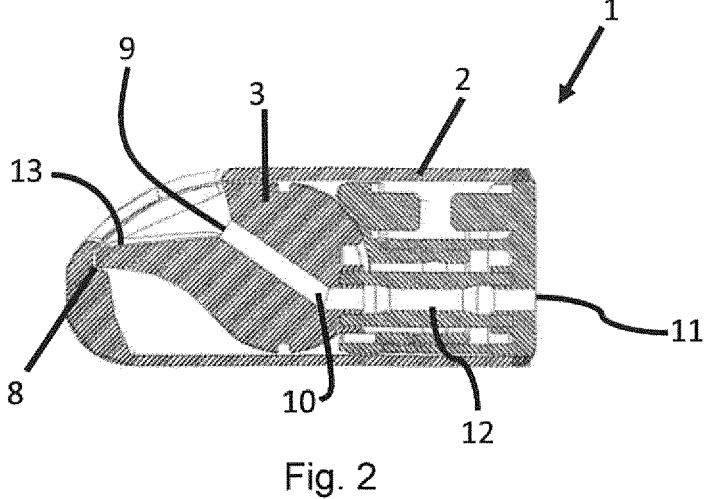
FIG. 2 shows a cross-sectional view of an implantable access device with a movable needle entrance and a first embodiment of locking means.

FIG. 2 shows a cross-sectional view of an implantable access device 1 for accessing the vascular system of a human or animal body, particularly subcutaneously implantable access port. The implantable access device 1 of FIG. 2 comprises a port body 2 with at least one outlet opening 11 connected or connectable to a catheter for accessing the vascular system of the human or animal body. The implantable access device further comprises a needle entrance 3 with at least one inlet opening 9 for receiving a needle, wherein the needle entrance 3 is connected to the port body and movable relative to the port body 2 between a first, unactuated operating condition and a second, actuated operating condition.

In the first, unactuated operating condition the passageway 10 from the inlet opening 9 of the needle entrance 3 to the outlet opening 11 of the port body 2 is closed by a valve 12 and in the second, actuated operating condition the passageway 10 from the inlet opening 9 of the needle entrance 3 to the outlet opening 11 of the port body 2 is opened by the valve 12.

The implantable access device 1 of FIG. 2 further comprises locking means 8 for locking the needle entrance 3 in the first, unactuated operating condition and in the second, actuated operating condition. The locking means 8 are activated by inserting the needle into the needle entrance 3 and applying a predetermined movement to the needle entrance 3 via the inserted needle and/or by applying a predetermined movement to the needle entrance 3 via the inserted needle and removing the needle from the needle entrance 3.

The locking means 8 shown in FIG. 2 first require a translational movement of the needle entrance 3 to the port body 2 and afterwards a pivoting movement of the needle entrance 3 to the port body 2 for transferring the needle entrance 3 from the first, unactuated operating condition to the second, actuated operating condition. For transferring the needle entrance 3 from the second, actuated operating condition back to the first, unactuated operating condition first a pivoting movement of the needle entrance 3 to the port body 2 followed by a translational movement of the needle entrance 3 to the port body 2 is necessary. Since the insertion of the needle into the needle opening 9 of the needle entrance 3 requires a diagonal movement of the needle the predetermined movement of the needle entrance 3 at least partially differs from the movement of the needle for inserting the needle into the needle entrance 3.

The needle entrance 3 comprises a funnel 13 for guiding the needle into the inlet opening 9 of the needle entrance.

The locking means 8 shown in FIG. 2 are implemented by a recess in the port body 2 into which a part of the needle entrance 3 engages in the first, unactuated operating condition. Further, the needle entrance 3 is pivotable in the port body 2 unless the part of the needle entrance 3 engages in the recess of the port body 2. Thus, for moving the needle entrance 3 from the first, unactuated operating condition to the second, actuated operating condition the part of the needle entrance 2 is first retracted from the recess of the port body 2 by a translational movement and afterwards the needle entrance 3 is pivoted relative to the port body 2. For moving the needle entrance 3 from the second, actuated operating condition to the first, unactuated operating condition the needle entrance 3 is first pivoted relative to the port body 2 and afterwards the part of the needle entrance 3 is moved into the recess of the port body 2 by a translational movement.

The locking in the first, unactuated operating condition is achieved by arranging the part of the needle entrance 3 in the recess of the port body 2. In the second, actuated operating condition the locking is achieved by a friction force between party of the needle entrance 3 and the inner surface of the port body 2.

The movement from the second, actuated operating condition to the first, unactuated operating condition can be supported by a spring between the port body 2 and the needle entrance 3. Preferably the spring is connected to or integrally formed with the valve mechanism 12 of the implantable access device 1.

Figure 3A:
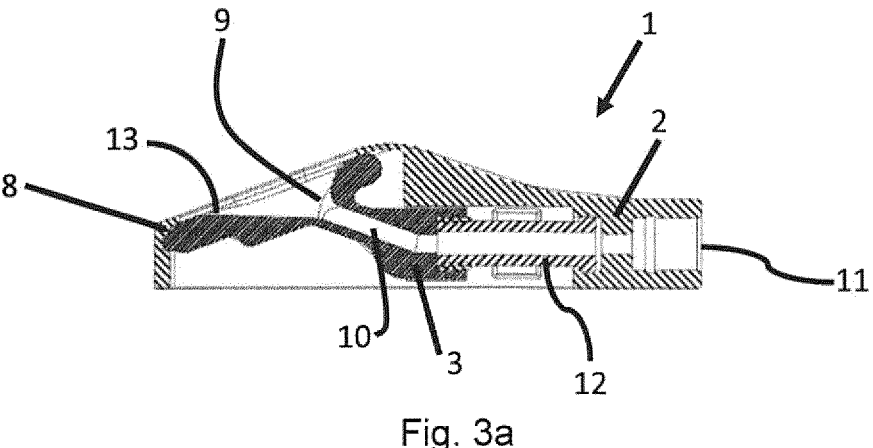

FIGS. 3a and 3b show cross-sectional views of an implantable access device 1 with a movable needle entrance 3 and a second embodiment of locking means 8. The locking 8 according to the second embodiment of shown in FIGS. 3a and 3b differs from the first embodiment mainly in that not pivoting movement of the needle entrance 3 is necessary for transferring the needle entrance 3 from the first, unactuated operating condition to the second, actuated operating condition. However, still in the first, unactuated operating condition a part of the needle entrance engages into a recess of the port body 2, as shown in the front part of the implantable access device at the left side of FIG. 3a.

FIG. 3b is a cross-sectional view of the implantable access device 1 from FIG. 3a outside of the middle of the port body, especially close to the side wall of the port body 2.

As can be seen from FIG. 3b the locking means according to the second embodiment further comprise a cam 14 on the needle entrance 3 and a corresponding recess 15 for receiving the cam 14 on the port body 2. In the second, actuated operating condition the cam 14 of the needle entrance 3 is received in the recess 15 of the port body 2 for locking the needle entrance 3 in the second, actuated operating condition.

The movement from the second, actuated operating condition to the first, unactuated operating condition can be supported by a spring between the port body 2 and the needle entrance 3. Preferably the spring is connected to or integrally formed with the valve mechanism 12 of the implantable access device 1.

The embodiment shown in FIGS. 3a and 3b further differs from the embodiment shown in FIG. 2 in that the overall design is flatter and stream lined. Especially the insertion angle in which the needle is inserted into the needle entrance 3 is smaller. Preferably the insertion angle of the needle entrance 3, in which the needle is inserted into the needle entrance 3, is between 15° and 40°, preferably between 25° and 30°.

FIG. 4a shows a needle entrance 3 for an implantable access device 1. On each side wall of the needle entrance a snap-fit 16 is arranged. FIG. 4b shows a detailed view of this snap-fit 16. The snap-fit 16 has a flexible part 18 and a hook part 19. The hook part 19 protrudes over the side wall of the needle entrance 3.

FIG. 4c shows a port body 2 for receiving the needle entrance 3 of FIG. 4a. The port body 2 comprises a protrusion 17 on each side wall. The snap-fit 16, particularly the hook 19 of the snap-fit 16 engages with the protrusion 17 in the second, actuated operating condition.

FIG. 4d shows an implantable access device 1 comprising a needle entrance 3 according to FIG. 4a and a port body 2 according to FIG. 4c. Other parts of the implantable access device 1, like e.g. the valve 12 between the port body 2 and the needle entrance 3 have been omitted due to simplicity. FIG. 4d shows the implantable access device in the first, unactuated operating condition. For moving the needle entrance 3 into the second, actuated operating condition the needle entrance is moved translational towards the outlet 11 of the port body. Thereby the valve 12 located between the port body 2 and the needle entrance 3 would be actuated and the passageway through the implantable access device 1 would be opened. The needle entrance 3 is moved so far towards the outlet 11 that the hooks 19 engage with the protrusions 17 of the port body 2. This is possible due to the flexible parts 18 of the snap-fit 16.

As can be seen from FIG. 4c or FIG. 4d the protrusion does not cover the total height of the port body 2 but ends above the base portion of the port body 2. By pivoting the needle entrance 3 it is possible to disengage the hooks 19 of the snap-fit 16 with the protrusions 17 of the port body 2, so that the needle entrance 3 can move back from the second, actuated operating condition to the first, actuated operating condition. This movement can be supported by a spring between the port body 2 and the needle entrance 3. Preferably the spring is connected to or integrally formed with the valve mechanism 12 of the implantable access device 1.

FIG. 5a shows a partial cross-sectional view of a fourth embodiment of locking means 8 for an implantable access device 1 comprising a port body 2 and a movable needle entrance 3. The main difference to the third embodiment of FIG. 4 is that the the snap-fits 16 have been arranged on the upper and lower sides of the needle entrance 3 and the protrusion of the port body 2 has been replaced by a recess 15 on the upper wall of the port body 2.

FIG. 5b shows a detailed view of the snap-fit 16 of FIG. 5a in the second, actuated operating condition. In this second, actuated operating condition the hook 19 of the snap-fit 16 engages into the recess 15 of the port body. 2. By pivoting the needle entrance 3 the hook 19 can be retracted from the recess 15 and the needle entrance can be transferred to the first, unactuated operating condition.

The lower wall of the port body 2 can comprise a further recess 15 for the lower snap-fit 16 in the first, unactuated operating condition, although this is not necessary. The lower snap-fit 16 has the main function to force the hook of the upper snap-fit 16 into the recess 15 in the second, actuated operating condition.

Figure 6A:
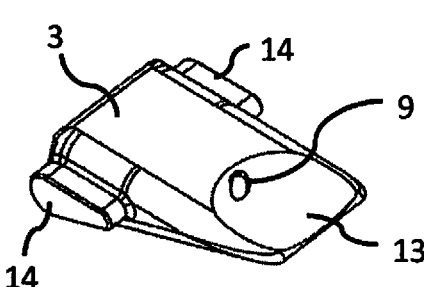
FIG. 6a, 6b show a fifth embodiment of locking means for an implantable access device.

FIG. 6a shows a needle entrance 3 for a fifth embodiment of a locking device 9 for an implantable access device 1. The needle entrance 3 comprises a cam 14 on each side wall. The cam 14 is triangular shaped, with rounded corners for s smooth relative movement between the needle entrance 2 and a port body 2, as shown e.g. in FIG. 6b.

Figure 6B:
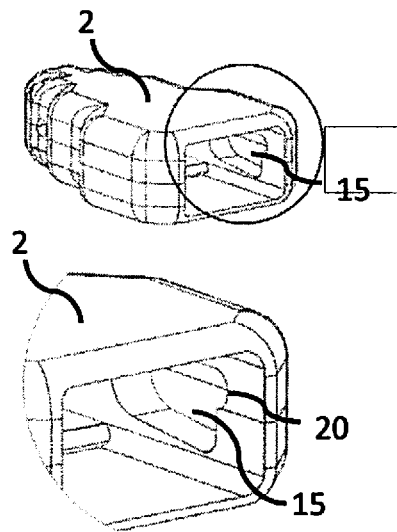

The port body 2 shown in FIG. 6b comprises in each side wall a recess 15 for guiding the cam 14 of the needle entrance 3. In the first, unactuated operating condition the pointed end of the triangular shaped cam 14 is arranged in the pit 20 of recess 15. Thereby the needle entrance 3 is locked in the first, unactuated operating condition.

To transfer the needle entrance 3 into the second, actuated operating condition the needle entrance 3 is first moved translational until the pointed end of the triangular cam 14 is outside of pit 20. Afterwards, the needle entrance is pivoted into the second, actuated operating condition. In this second, actuated operating condition the needle entrance 3 is locked by a friction force between the cam 14 and the side wall of recess 15.

Alternatively, the recess 15 can comprise a further pit 20 for locking the cam in the second, actuated operating condition by a further translational movement, so that the pointed end of the triangular cam 14 is arranged in the second pit 20. In this embodiment the recess 15 is shaped like a heart.

The aforementioned locking means 8 are only illustrative and the skilled person can combine features of the different described locking means 8 with each other or can implement other locking means into the implantable access device within the scope of this invention. In general, every bistable locking means 8 can be used with an implantable access device 1, including a ballpoint pen mechanism or a SD-slot mechanism. Preferably push-push locking means 8 are used, with a translational and/or pivoting movement for actuation.

Figure 7:
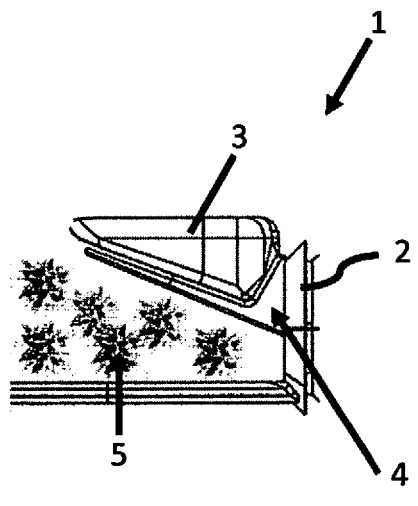
FIG. 7 shows the implantable access device from FIG. 1a with tissue growth.

FIG. 7 shows a detailed view of the implantable access device 1 from FIG. 1a in the area or volume of the movement between the needle entrance 3 with the receptacle 4 to the port body 2. As has been indicated by numeral 5 tissue has started to grow into the area or volume where the movement between the needle entrance 3 with the receptacle 4 and the port body 4 takes place. This tissue 5 would be pinched by pivoting the needle entrance 3 with the receptacle 4 relative to the port body 2 to the second, actuated operating condition as shown FIG. 1b and thereby eventually causing pain to the patient and/or blocking the relative movement between the needle entrance 3 with the receptacle 4 to the port body 2.

Figure 8A:
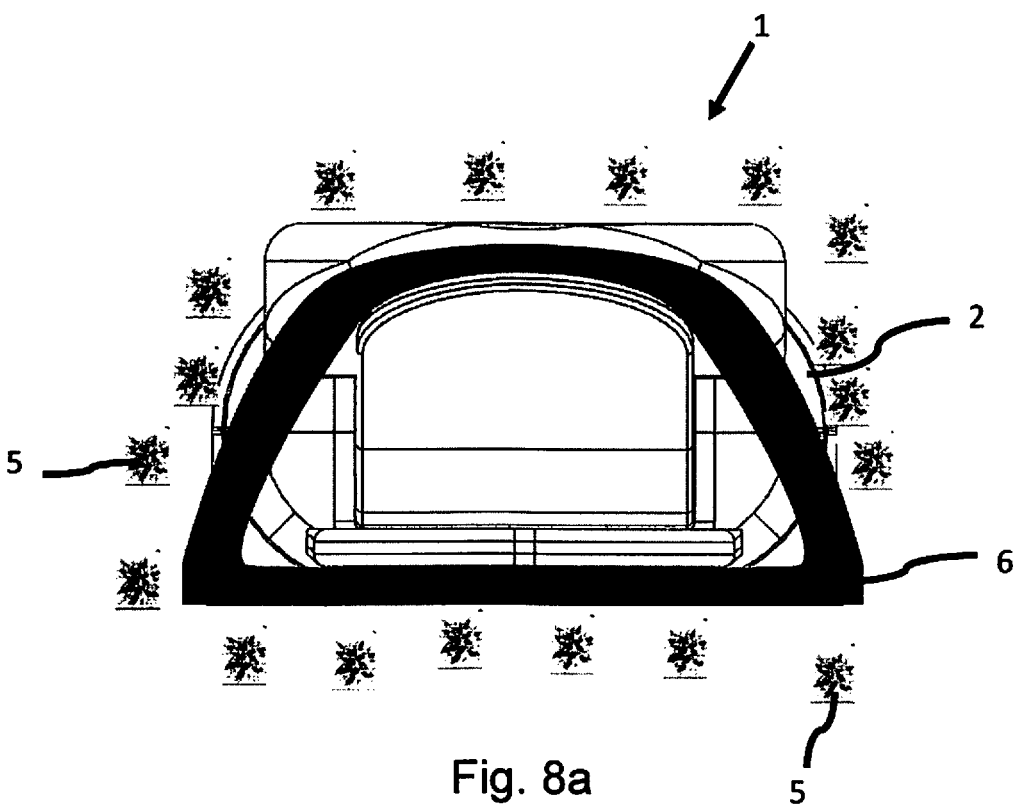
FIG. 8a shows a cross-sectional view of an implantable access device with a flexible socket in a first, unactuated operating condition.

FIG. 8a shows a cross-sectional view an implantable access device 1 with a flexible socket 6 in a first, unactuated operating condition. The flexible socket 6 is arranged between the needle entrance 3 with the receptacle 4 and the port body 2. The flexible socket 6 at least covers the area or volume where the needle entrance 3 and the receptacle 4 move relative to the port body 2 to prevent tissue growth in this area or volume, as indicated by numeral 5 in FIG. 8a outside the flexible socket 6. As can be seen from the cross-sectional view of FIG. 8a the flexible socket 6 is hollow.

Preferably the flexible socket 6 has a first opening for connecting the flexible socket 6 to the port body 2 and a second opening for connecting the flexible socket 6 to the needle entrance 3 and/or receptacle 4.

For a secure fixing of the flexible socket 6 to the port body 2 the first opening of the flexible socket 6 is smaller, e.g. 10% to 20% smaller, than a corresponding connecting portion of the port body 2.

The second opening of the flexible socket 6 is for example clamped between the needle entrance 3 and the receptacle 4, as will be explained later with respect to FIGS. 10a and 10b.

Preferably the flexible socket 6 is made of silicone.

Figure 8B:
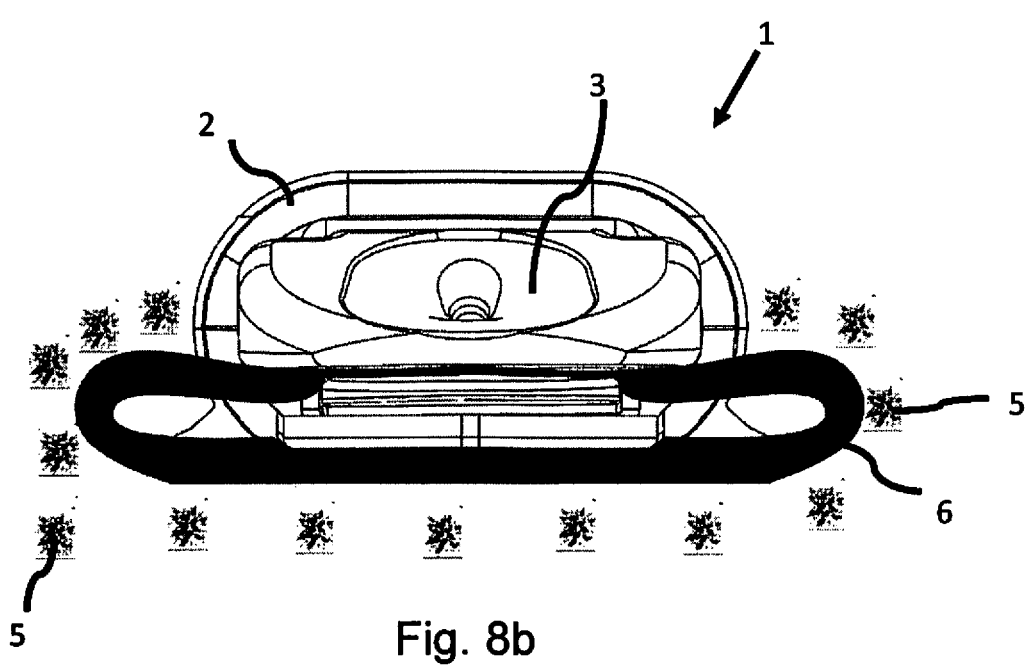
FIG. 8b shows a cross-sectional view of the implantable access device from FIG. 8a in a second, actuated operating condition.

FIG. 8b shows the implantable access device of FIG. 8a in a second, actuated operating condition. In the shown second, actuated operating condition the needle entrance 3 with the receptacle 4 have been pivoted relative to the port body 2, thereby deforming the flexible socket 6. The deformed flexible socket 6 pushes the surrounding tissue away from the implantable access device 1, especially in the area or volume of relative movement between the needle entrance 3 with receptacle 4 and the port body 2.

Figure 9:
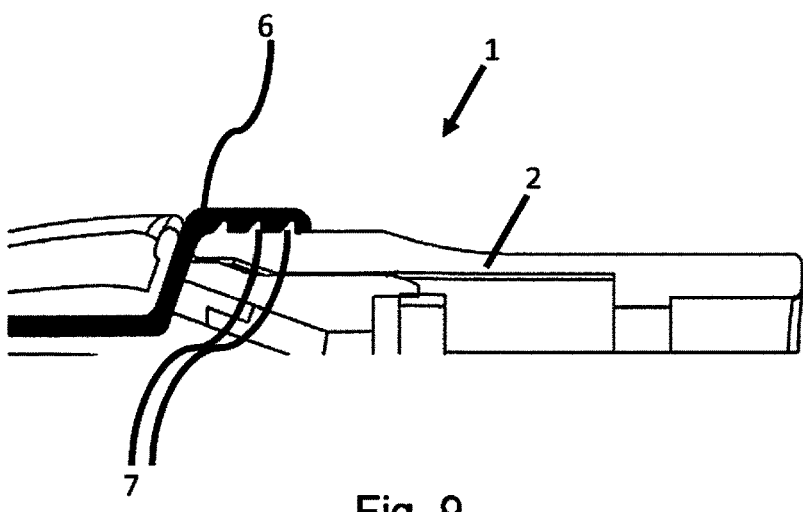
FIG. 9 shows a detailed view of a barb connection between a flexible socket and a port body.

FIG. 9 shows a detailed view of a barb connection 7 between a flexible socket 6 and a port body 2. The flexible socket 6, particularly the first opening of the flexible socket 6, and the connecting portion of the port body 2 have corresponding surfaces, so that the contact area and thus, the fixing is enhanced. Particularly preferred the corresponding surfaces comprise protrusions and recesses, like the barb connection 7 shown in FIG. 9. The shown barb connection 7 has the additional advantage that only a movement of the flexible socket 6 to the port body 2 in the assembly direction is possible, where a movement in the opposite direction is prevented by the barb connection 7.

Figure 10A:
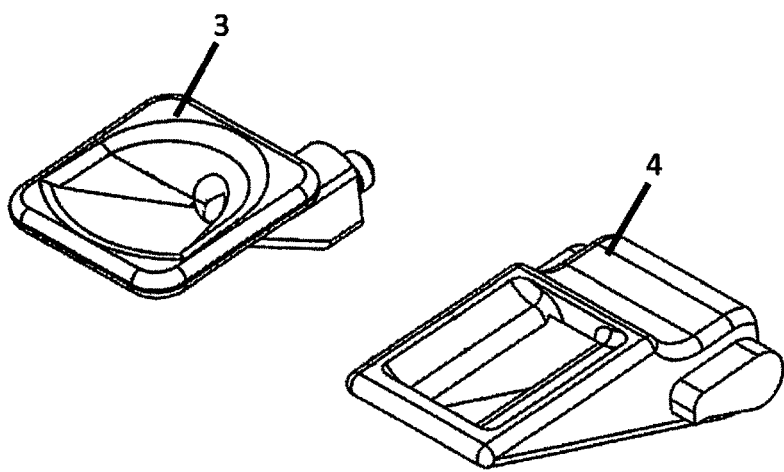
FIG. 10a shows a detailed view of a needle entrance and a receptacle.

FIG. 10a shows a detailed view of a needle entrance 3 and a receptacle 4. The needle entrance 3 and the receptacle 4 are designed such that the needle entrance 3 can be introduced and fixed inside the receptacle 4. The receptacle 4 is movably connected to the port body 2 of the implantable access device 1, to define the relative movement between the needle entrance 3 with the receptacle 4 and the port body 2 from the first, unactuated operating condition to the second, actuated operating condition.

Figure 10B:
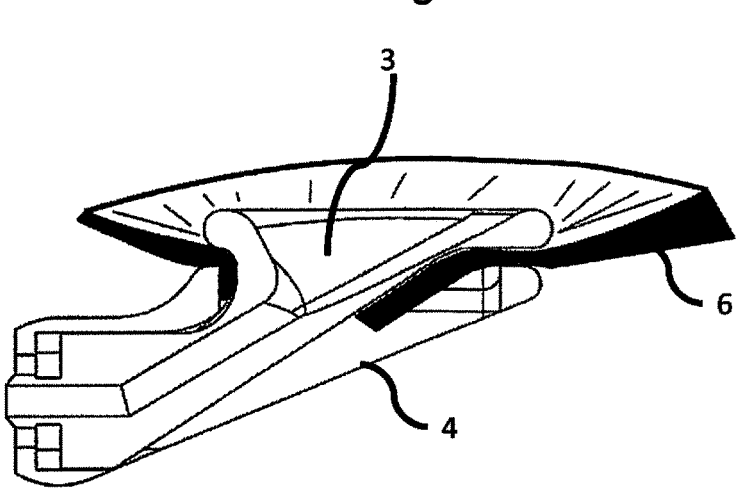
FIG. 10b shows a detailed cross-sectional view of a flexible socket clamped between a needle entrance and a receptacle.

FIG. 10b shows a detailed view of the needle entrance 3 introduced into the receptacle 4 of FIG. 10a. Between the needle entrance 3 and the receptacle 4 the flexible socket 6 has been at least partially, preferably the second opening of the flexible socket 6, clamped, to fix the flexible socket 6 to the needle entrance 3 and receptacle 4.

LIST OF NUMERALS

1 implantable access device
2 port body
3 needle entrance
4 receptacle
5 tissue
6 flexible socket
7 barb connection
8 locking means
9 inlet opening
10 passageway
11 outlet opening
12 valve
13 funnel
14 cam
15 recess
16 snap-fit
17 protrusion
18 flexible part
19 hook
20 pit

What is claimed is:

1. An implantable access device to access a vascular system of a human or animal body, comprising:
   a port body with at least one outlet opening connected or connectable to a catheter to accessing the vascular system of the human or animal body;
   a needle entrance formed entirely by a single structure with at least one inlet opening to receive a needle, wherein the needle entrance is connected to the port body and movable relative to the port body between a first, unactuated operating condition and a second, actuated operating condition, and wherein at least a portion of the needle entrance is external to the port body; and
   at least one bistable locking mechanism configured to lock the needle entrance to the port body in the first, unactuated operating condition and configured to further lock the needle entrance to the port body in the second, actuated operating condition,
   wherein the at least one bistable locking mechanism is activated by a predetermined movement of the needle entrance relative to the port body and the predetermined movement is achieved by at least one of (1) inserting the needle into the needle entrance and moving the needle entrance via the inserted needle, and (2) moving the needle entrance via an inserted needle and removing the inserted needle from the needle entrance, and wherein the predetermined movement applied to the needle entrance comprises a pivoting movement and a translational movement.

2. The implantable access device according to claim 1, wherein the predetermined movement applied to the needle entrance at least partially differs from a movement of the needle for inserting the needle into the needle entrance.

3. The implantable access device according to claim 1, wherein an insertion angle of the needle entrance, in which the needle is inserted into the needle entrance, is between 15° and 40°.

4. The implantable access device according to claim 3, wherein the insertion angle of the needle entrance is between 25° and 30°.

5. The implantable access device according to claim 1, wherein the needle entrance comprises a funnel to guide the needle into the needle entrance.

6. The implantable access device according to claim 1, wherein the at least one bistable locking mechanism comprises at least one of: (1) a cam on the needle entrance and a corresponding recess to guide the cam on the port body, and (2) a cam on the port body and a corresponding recess to guide the cam on the needle entrance.

7. The implantable access device according to claim 6, wherein the cam is shaped rectangular or triangular.

8. The implantable access device according to claim 7, wherein the cam has rounded corners.

9. The implantable access device according to claim 6, wherein the recess has at least one pit to receive the cam in at least one of the first, unactuated operating condition and the second, actuated operating condition.

10. The implantable access device according to claim 9, wherein the recess is heart shaped.

11. The implantable access device according to claim 6, wherein the recess has one pit to receive the cam in the first, unactuated operating condition and another pit to receive the cam in the second, actuated operating condition.

12. The implantable access device according to claim 11, wherein the recess is heart shaped.

13. The implantable access device according to claim 1, wherein the at least one bistable locking mechanism comprises a push-push locking mechanism.

14. The implantable access device according to claim 1, wherein the at least one bistable locking mechanism comprises a snap fit connection.

15. The implantable access device according to claim 14, wherein the snap fit connection comprises a snap on the needle entrance and at least one recess or protrusion on the port body to receive or engage with the snap, to lock the needle entrance in the first, unactuated operating condition and in the second, actuated operating condition.

16. The implantable access device according to claim 1, wherein the at least one locking bistable mechanism comprises a spring to lock the at least one bistable locking mechanism in the first, unactuated operating condition and in the second, actuated operating condition.

17. The implantable access device according to claim 16, wherein the spring is connected to or integrally formed with a valve mechanism of the implantable access device.

18. The implantable access device according to claim 1, wherein the at least one bistable locking mechanism creates at least one of an audio feedback and a haptic feedback when being locked in at least one of the first, unactuated operating condition and the second, actuated operating condition.

19. The implantable access device according to claim 18, wherein the audio feedback comprises a sound and the haptic feedback comprises a vibration.

* * * * *